United States Patent [19]

White et al.

[11] Patent Number: 5,352,351

[45] Date of Patent: Oct. 4, 1994

[54] BIOSENSING METER WITH FAIL/SAFE PROCEDURES TO PREVENT ERRONEOUS INDICATIONS

[75] Inventors: Bradley E. White, Indianapolis; Robert A. Parks, Springport; Paul G. Ritchie, Indianapolis; Vladimir Svetnik, Carmel, all of Ind.

[73] Assignee: Boehringer Mannheim Corporation, Indianapolis, Ind.

[21] Appl. No.: 73,180

[22] Filed: Jun. 8, 1993

[51] Int. Cl.$^5$ ............................................. G01N 27/26
[52] U.S. Cl. ................................... 204/406; 204/407; 204/403
[58] Field of Search ................... 204/406, 407, 403; 435/817

[56] References Cited

U.S. PATENT DOCUMENTS

| 4,420,564 | 12/1983 | Tsuji et al. | 204/403 |
|---|---|---|---|
| 4,940,945 | 7/1990 | Littlejohn et al. | 324/438 |
| 4,999,582 | 3/1991 | Parks et al. | 204/406 |
| 5,053,199 | 10/1991 | Keiser et al. | 422/68.1 |
| 5,108,564 | 4/1992 | Szuminsky et al. | 204/403 |

FOREIGN PATENT DOCUMENTS 0471986 2/1992 European Pat. Off. .

*Primary Examiner*—John Niebling
*Assistant Examiner*—Bruce F. Bell
*Attorney, Agent, or Firm*—Perman & Green

[57] ABSTRACT

A biosensing meter receives a sample strip that includes electrically isolated sense and excitation electrodes bridged by a reaction zone. When a drop of biological sample fluid is placed in the reaction zone, a plurality of fail/safe tests are performed. A drop size test is performed by a circuit that detects the size of the drop placed in the reaction zone. The circuit both detects that a drop has been placed in the reaction zone and further measures a test current level, after a delay, to determine that the drop size is sufficient to enable hydration of reactants in the reaction zone. Subsequently, during the reaction, a "delta" current change is measured at succeeding sample time. This test measures the difference between succeeding current samples during a measurement time. If each succeeding sample is not less than preceding sample by a delta value, a determination is made that the current is not monotonically decreasing and the test is aborted. At the termination of the measurement time, a current sum test is performed wherein a processor calculates a linear sum of all sample test currents and calculates a ratio between that sum and the last current sample. If that ratio matches a pre-calculated constant for the Cottrell relationship, then it is known that the measurement values exhibit the Cottrell relationship.

10 Claims, 4 Drawing Sheets

BIOSENSING METER WITH FAIL/SAFE PROCEDURES TO PREVENT ERRONEOUS INDICATIONS

FIELD OF THE INVENTION

This invention relates to biosensing meters that employ disposable sample strips, and more particularly, to fail/safe systems and procedures for preventing such meters from issuing erroneous results.

BACKGROUND OF THE INVENTION

Biosensing instruments that employ disposable sample strips enjoy wide consumer acceptance. Such instruments are employed for the detection of various analyte levels in blood samples, e.g., glucose and cholesterol. In general, such instruments provide accurate readings if the user is careful to follow the instrument's directions. Often however, the user is careless in the use of either the sample strip or the instrument and an erroneous reading results. Accordingly, significant efforts have been taken by instrument manufacturers to reduce the potential for errors during the use of such instruments.

Even if a biosensing instrument and sample strips are employed properly, the presence of a manufacturing defect in either will cause erroneous readings. Thus, while great care is taken in the production of such instruments and sample strips, there is a need to incorporate analytical procedures in the instrument that enable instrument malfunctions, sample strip irregularities and user errors to be detected so as to prevent erroneous analyte readings.

The prior art includes a number of disclosures of biosensing instruments that employ disposable sample strips. In U.S. Pat. No. 5,108,564 to Szuminsky et al., a biosensing instrument is disclosed that measures glucose concentrations in blood. The instrument depends upon a reaction wherein glucose, in the presence of an enzyme, catalyzes a reaction of potassium ferricyanide to potassium ferrocyanide. After the reaction has completed, a voltage is applied across a reaction zone and causes a reversal of the reaction with an accompanying generation of a small, but measurable current. That current is termed the Cottrell current and, in dependence upon the concentration of glucose in the reaction zone, follows a predetermined curve during the reverse reaction. A reading of the Cottrell current is converted into an indication of glucose concentration. The instrument also senses an impedance across the reaction zone and determines when a blood sample has been emplaced therein by detecting a sudden change in current flow. At such time, an incubation period is commenced, followed by application of a potential across the reaction zone and measurement of the Cottrell current.

European Patent Application 0 471 986 A2 of Tsutsumi et al. discloses a blood glucose measurement system that employs disposable sample strips. The Tsutsumi et al. system detects the presence of a blood sample by sensing a resistance across a pair of electrodes. It further employs a plurality of sample-like strips, each having a specific resistance value which distinguishes it from other strips. Each of those strips has a particular application, i.e., for use during an adjustment mode of the instrument, during an error compensation mode, during a calibration mode, etc.

U.S. Pat. No. 4,999,582 to Parks et al., assigned to the same Assignee as this application, describes a biosensor electrode excitation circuit for determining if a sample strip has been properly inserted into a meter and if at least one electrode on the sample strip exhibits a proper level of contact resistance.

U.S. patent application Ser. No. 07/451,309, filed Dec. 15, 1989 to White, entitled "Biosensing Instrument and Method" and assigned to the same assignee as this application, teaches a biosensing instrument which employs the "Cottrell" curve relationship to determine glucose concentrations. In that instrument, current flow is proportional to the concentration of an analyte in the test cell; however, when something is amiss in the test cell, the current that results may bear no relationship whatever to analyte concentration. White found that a relationship exists that enables a determination to be made whether current flow through a reaction zone is, in fact, following the Cottrell relationship. More specifically, the ratio of the square roots of succeeding sample times, for all analyte concentration curves, has been found to inversely approximate the ratio of the measured Cottrell currents at those same sample times. If over succeeding time periods, the ratios are equal (within limits), the measurement system is properly following the Cottrell relationship. If the ratios found are not equal, the measurement is disregarded.

U.S. Pat. No. 4,940,945 to Littlejohn et al. describes an interface circuit for use in a biochemical sensing instrument. A disposable cartridge is employed that includes a pair of electrodes across which resistance measurements are taken. Circuitry is disclosed for sensing the presence of a fluid sample by an initial resistance measurement, and also the level of fluid in the cartridge.

U.S. Pat. No. 4,420,564 to Tsuji et al. describes a blood sugar analyzer that employs a reaction cell having a fixed enzyme membrane sensor and a measuring electrode. The Tsuji et al. system includes several fail/safe procedures, one to determine that the reaction is taking place within specifically defined temperature limits and a second to determine that the reaction current remains within a predetermined range.

The above noted prior art indicates that biosensing meters have had the ability to determine when a biological sample is placed in a reaction zone. However, the prior art has not addressed the problem of the presence of an insufficient amount of the sample to fully wet enzymatic reactants present in a reaction zone. Furthermore, while a test is available to determine that a reaction is following the Cottrell relationship (as described in the aforesaid patent application to White), additional, confirming, tests are desirable to assure that the reaction is in fact, following the Cottrell relationship.

Accordingly, it is an object of this invention to provide a biosensing meter with means for performing a plurality of fail/safe tests during the course of an analysis of a biological sample.

It is another object of this invention to provide a biosensing meter with means for determining that adequate amount of a sample has been placed in a sample strip's reaction zone.

It is a further object of this invention to provide means for determining that a biological sample is reacting in accordance with the Cottrell relationship during the course of the reaction and, if not, causing resulting readings to be ignored.

SUMMARY OF THE INVENTION

A biosensing meter receives a sample strip that includes electrically isolated sense and excitation electrodes bridged by a reaction zone. When a drop of biological sample fluid is placed in the reaction zone, a plurality of fail/safe tests are performed. A drop size test is performed by a circuit that detects the size of the drop placed in the reaction zone. The circuit both detects that a drop has been placed in the reaction zone and further measures a test current level, after a delay, to determine that the drop size is sufficient to enable hydration of reactants in the reaction zone. Subsequently, during the reaction, a "delta" current change is measured at succeeding sample time. This test measures the difference between succeeding current samples during a measurement time. If each succeeding sample is not less than preceding sample by a delta value, a determination is made that the current is not monotonically decreasing and the test is aborted. At the termination of the measurement time, a current sum test is performed wherein a processor calculates a linear sum of all sample test currents and calculates a ratio between that sum and the last current sample. If that ratio matches a pre-calculated constant for the Cottrell relationship, then it is known that the measurement values exhibit the Cottrell relationship.

DETAILED DESCRIPTION OF THE INVENTION

Figure 1:
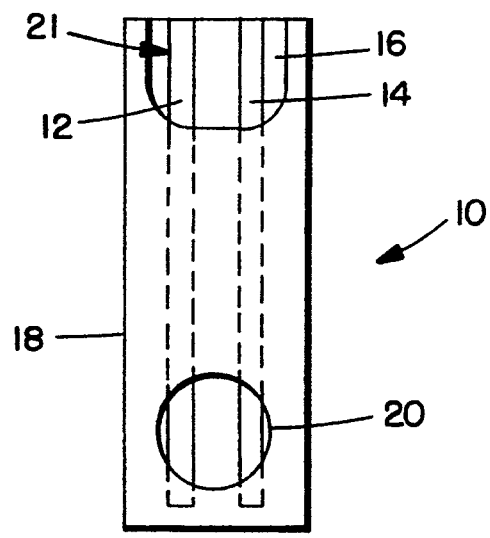
FIG. 1 is a plan view of a sample strip.

Referring to FIG. 1, a sample strip 10 comprises two electrodes, i.e., sense electrode 12 and excitation electrode 14. Those electrodes are supported on a polymeric sheet 16 and a cover sheet 18 is provided thereover and has openings 20 and 21 which expose portions of electrodes 12 and 14. Opening 20 creates a sample well and defines a reaction zone between sense electrode 12 and excitation electrode 14. A layer (not shown) of enzymatic reactants overlays electrodes 12 and 14 in opening 20 and provides a substrate on which an analyte-containing fluid sample emplaced. In this example, it will be assumed that the analyte-containing sample is a drop of blood that is being subjected to a glucose determination. Opening 21 exposes electrodes 12 and 14 so that when sample strip 10 is inserted into a biosensing meter, electrical connection can be made thereto.

Figure 2:
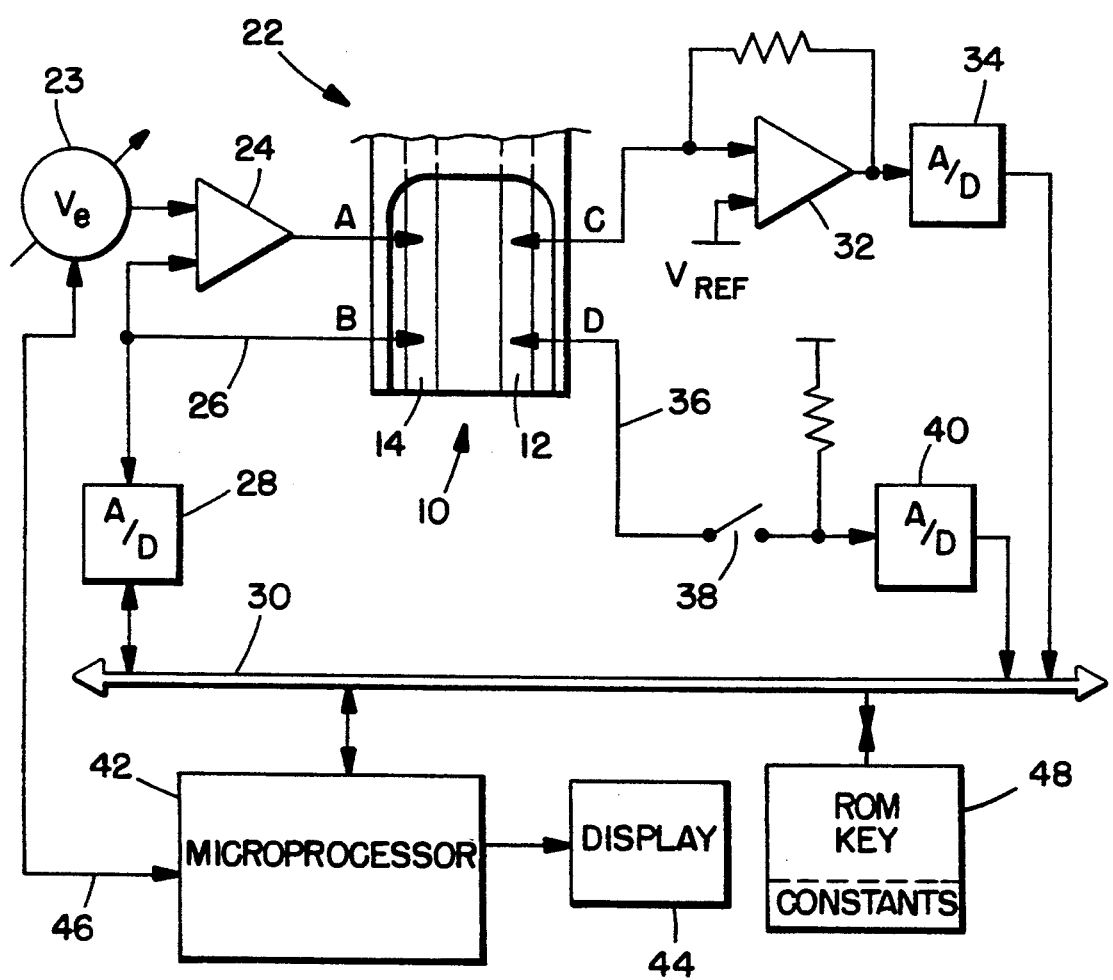
FIG. 2 is a circuit/block diagram of a biosensing meter that embodies the invention hereof.

In FIG. 2, a schematically illustrated biosensing meter 22 includes a window (not shown) for accepting sample strip 10 and for enabling electrical connection to be made between excitation electrode 14 and a pair of contacts A and B and between sense electrode 12 and a pair of contacts C and D. Excitation electrode 14, if it is continuous and properly inserted, electrically connects contacts A and B together. Similarly, sense electrode 12 electrically shorts contacts C and D if sample strip 10 is properly inserted. Contacts A, B and C, D are spaced apart within biosensing meter 24 and enable a determination to be made that a sample strip 10 has been properly inserted into meter 22 and that its electrodes reflect proper impedance states. Once such determinations indicate a properly inserted sample strip (with appropriate excitation and sense electrodes), sample strip 10 may be dosed by application of a drop of blood to well 20 and subsequent measurements made.

An excitation supply 23 has its excitation voltage $V_e$ applied via operational amplifier 24 and contact A to excitation electrode 14. A second input to operational amplifier 24 is fed from contact B via line 26. That same input is applied to analog to digital (A/D) converter 28 which, in turn, applies its digitized output onto bus 30. On the sense side of biosensing meter 22, contact C is connected to one input of operational amplifier 32. Another input to operational amplifier 32 is connected to a reference potential. The output from operational amplifier 32 is applied via A/D converter 34 to bus 30.

Contact D is connected via conductor 36 and a multiplex switch 38 to A/D converter 40 whose output is, in turn, applied to bus 30. A supply voltage V is connected via a resistor to an input to A/D converter 40. Switch 38 is closed when meter 22 is initially powered so as to enable a determination to be made of the proper insertion of sense electrode 12. Once that determination is made, switch 38 is opened, thereby disabling the input to A/D converter 40.

A microprocessor 42 and an allied display 44 is connected to bus 30 and controls the overall operation of biosensing meter 22. Microprocessor 42 also, via line 46, controls the excitation voltage that is applied from supply 23 through operational amplifier 24 to contact A. An insertable read only memory (ROM) key 48 is interconnectable with bus 30 and enables the insertion of constants and other test parameters for use with a group of sample strips 10.

The operation of biosensing meter 22 in the sensing of proper insertion of sample strip 10 and the continuity of excitation and sense electrodes 14 and 12, respectively, is described in detail in copending patent application Ser. No. 08/073,178 White et al., entitled "Biosensing Meter with Disposable Sample Strips and Check Strips for Meter Quality Determinations", filed on even date herewith. The disclosure of the White et al. patent application is incorporated herein by reference.

Figure 3:
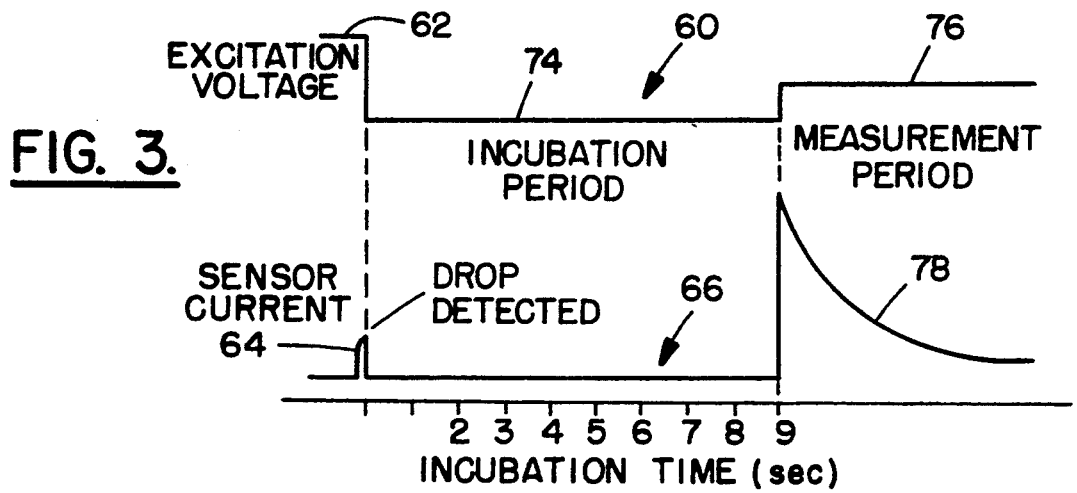
FIG. 3 is a wave form diagram illustrating both the excitation voltage applied to the excitation electrode on the sample strip of FIG. 1 and the resulting sense current from the sense electrode on the sample strip.
Figure 4:
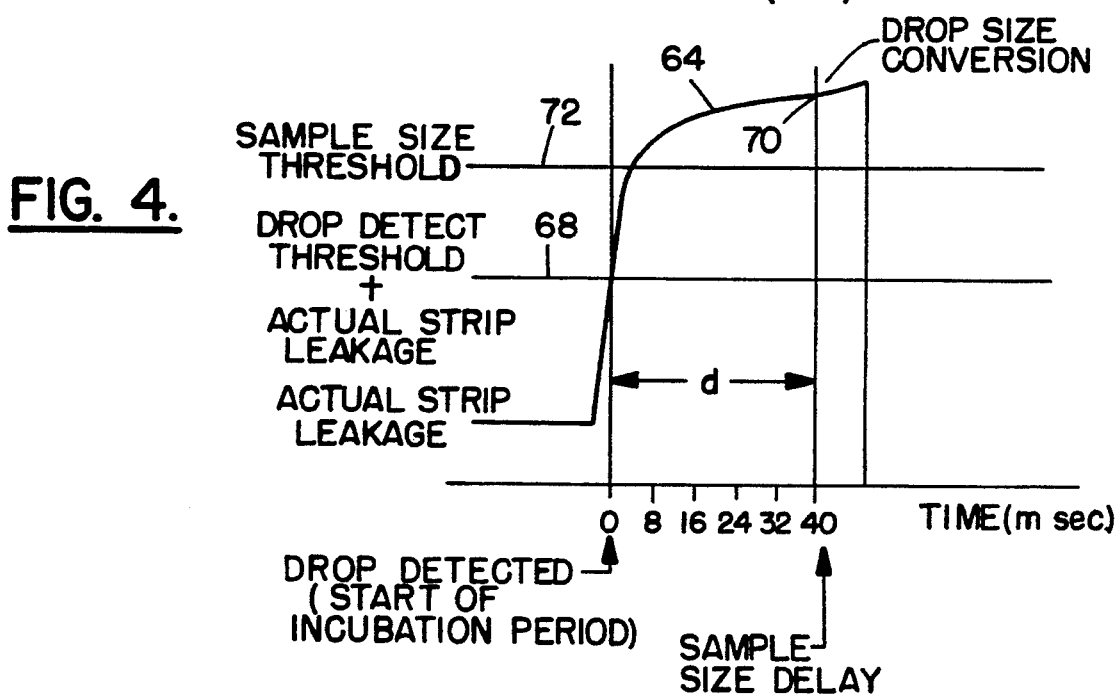
FIG. 4 is an expanded view of the sense current waveform that occurs when a drop of analyte is initially detected.

Once microprocessor 42 determines that a sample strip is properly inserted and that sense and excitation electrodes 12 and 14 exhibit proper electrode continuities, excitation supply 23 is caused to apply an excitation voltage $V_e$ to operational amplifier 24 and, in turn, to contact A. The waveform of excitation voltage $V_e$ is indicated in FIG. 3 by trace 60. Initially, a high level voltage 62 is applied to excitation electrode 14 and a measurement is made of leakage current between excitation electrode 14 and sense electrode 12. If the leakage current is found to be within an acceptable range, microprocessor 42 indicates (on display 44) that the user may apply a drop of blood to well 20. Upon application of the drop of blood, an immediate drop in resistance (i.e. an increase in current) is sensed between electrodes 12 and 14. The resulting output from operational amplifier 32 is indicated as pulse 64 of signal trace 66. An expanded view of pulse 64 is shown in FIG. 4.

As pulse 64 passes through a first threshold 68, microprocessor 42 determines that a drop of blood has been detected. The level of threshold 68 is set at a low level so as to rapidly detect when a strip 10 is dosed with a blood sample and to thereby clearly indicate the commencement of an incubation period. Upon pulse 64 passing through threshold 68, a time delay d is commenced in microprocessor 42, at the termination of which a second measurement is taken of waveform 64 (at time 70). Time delay d is employed to enable the drop of blood to wet the entire area within well 20. If the current sensed at time 70 is below a sample size threshold 72, the test is aborted as the volume of the blood drop is determined to be insufficient to assure complete hydration of the enzymatic reactants within well 20. By contrast, if the voltage (current) sensed at time 70 exceeds sample size threshold 72, the reaction is permitted to continue.

Shortly thereafter, microprocessor 42 causes the excitation voltage $V_e$ from supply 22 to be removed from contact A (trace 74 in FIG. 3). Trace 74 is the "incubation" time and extends for a sufficient period of time to enable an enzymatic reaction to occur between the blood drop and the enzymes in well 20.

Figure 5:
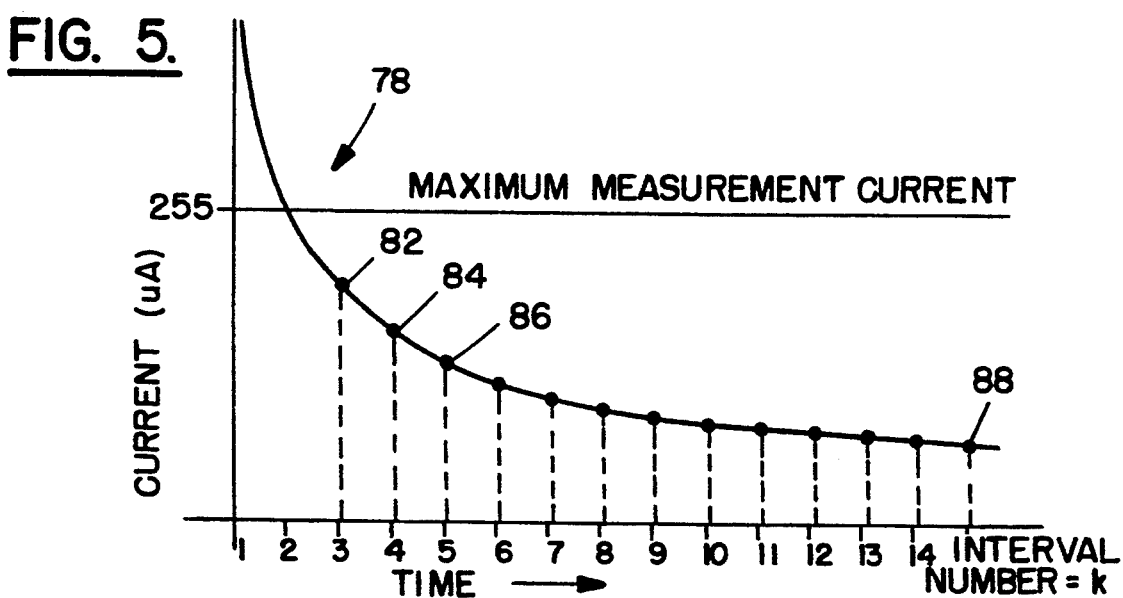
FIG. 5 is an expanded view of a plurality of measured currents detected during the measurement period, which currents follow an expected Cottrell relationship.

Referring back to FIG. 3, at the termination of the incubation time an excitation voltage $V_e$ (trace 76) is again applied to contact A causing a reverse reaction in well 20. The resulting current (trace 78) is sensed at sense electrode 12. FIG. 5 is an enlarged showing of trace 78 and illustrates the classic Cottrell relationship exhibited by current flow during the above noted reverse reaction. In FIG. 5, sense current is plotted against elapsed time and, as known in the art, trace 78 is either displaced upwardly or downwardly in the plot of FIG. 5, depending upon glucose concentration. During the period of trace 78, microprocessor 42 records a plurality of current measurement values, each value taken a time interval with k being the interval count. Those measurements both enable a glucose determination to be made, and are used to assure that trace 78 is, in fact, following the Cottrell relationship.

Assuming a glucose concentration determination is to be made, well 20 includes the following reactants: an enzyme, an electrolyte, a mediator, film formers, and a buffer. For instance, the enzyme may be glucose oxidase (or glucose dehydrogenase); the buffer may be organic or inorganic; the electrolyte may be potassium chloride or sodium chloride; the mediator is preferably potassium ferricyanide and the film formers comprise gelatin and propiofin. If the test cell is to be employed for a cholesterol concentration determination, the enzyme would preferably be cholesterol oxidase with or without a cholesterol esterase additive. The buffer is preferably inorganic and includes an electrolyte such as potassium chloride or sodium chloride. In this case, two mediators are used, i.e. ferricyanide and quinones, and are placed in a gelatin film, as indicated above.

As the chemistries employed by this system are known in the art, they will not be described in further detail. Suffice to say that glucose concentration is determined by initially emplacing in well 20, a sample of blood. The glucose within the sample causes a forward reaction of potassium ferricyanide to potassium ferrocyanide. When the forward reaction has proceeded to completion during the incubation period, a subsequent application of a voltage (trace 76) to excitation electrode 14 will see the creation of a small current at sense electrode 12 that results from a reverse reaction of potassium ferrocyanide back to potassium ferricyanide. The flow of electrons during the reverse reaction (trace 78) is sensed and measured.

Figure 6:
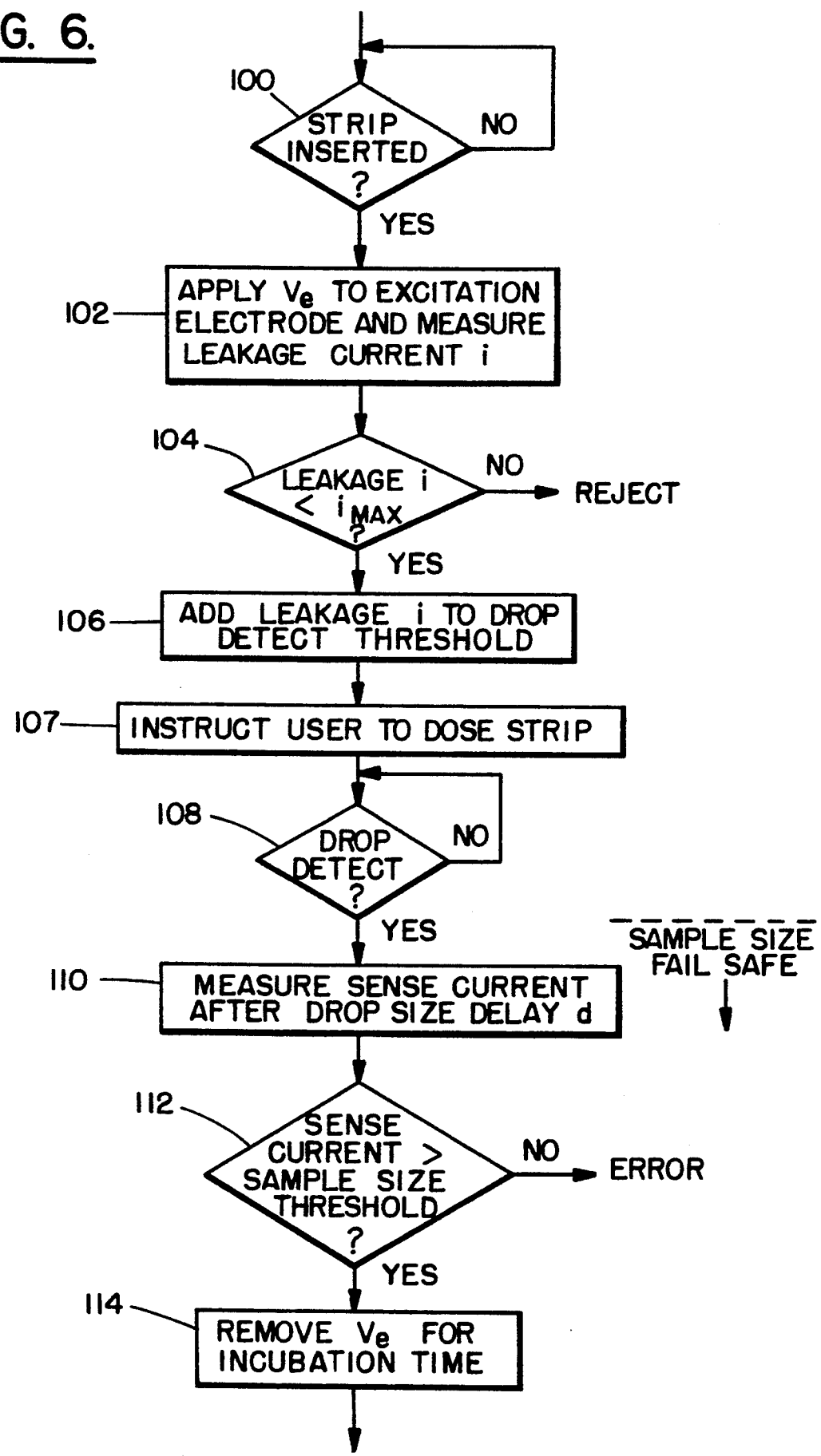
FIGS. 6 and 7 are high level flow diagrams illustrating the sample size, delta and current sum fail/safe tests performed by the circuit of the FIG. 2.
Figure 7:
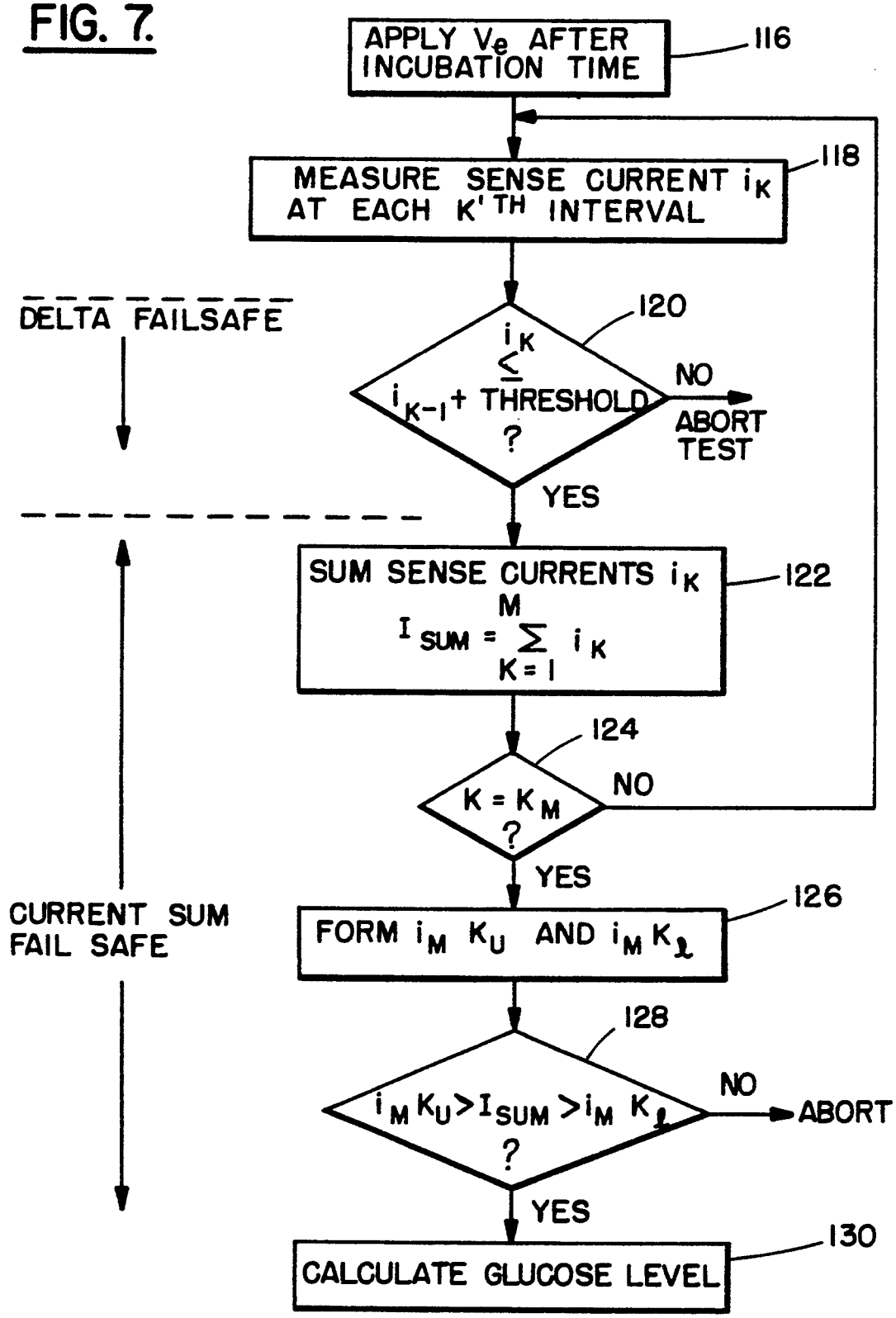

Turning to FIGS. 6 and 7, the operation of the meter of FIG. 2 will be described. Initially (FIG. 6), microprocessor 42 detects an insertion of a sample strip 10 by sensing the electrical shorting of contacts A and B and contacts C and D (decision box 100). Until microprocessor 42 detects the presence of sample strip 10, the procedures recycles. Upon sensing the presence of sample strip 10 and determining that the contact resistances between contacts A, B and C, D, respectively, are within proper limits, microprocessor 42 causes excitation supply 23 to apply excitation voltage level 62 (FIG. 3) to excitation electrode 14. This application occurs prior to any dosage of sample strip 10 and enables the leakage current (if any) between electrodes 12 and 14 to be measured. Simultaneously, microprocessor 42 obtains a leakage current threshold value ($i_{max}$) from ROM key 48 and compares its value with a measured leakage current i fed from A/D converter 34 (boxes 102 and 104). If the leakage current i is less than the threshold leakage current value ($i_{max}$) the procedure continues, as the leakage current is within limits. If not, the sample strip is rejected.

At this point, microprocessor 42 enters a "drop detect" state wherein it is determined when a blood drop has been positioned in well 20 and whether the volume of the blood drop is sufficient to completely wet the enzymatic reactants positioned therein. Initially, microprocessor 42 loads a pair of constants from ROM key 48, i.e., a drop detect threshold value and a sample size threshold value (72). Microprocessor 42 then adds the measured leakage current value i to the drop detect threshold value to determine drop detect threshold 68 shown in FIG. 4 (box 106). Then, microprocessor 48 causes display 44 to indicate to the user that the sample strip is ready for dosing.

Microprocessor 42 now enters a wait state (with excitation voltage level 62 continuing to be applied to excitation electrode 14). When a blood drop is applied to well 20, a current increase is sensed (pulse 64 in FIG. 4), and when the measured current value exceeds threshold 68, a drop is indicated as having been detected (decision box 108). An incubation timing period now commences which, for example, may be nine seconds. A sample size delay period d is also started, after which a second measurement is taken of pulse 64 (box 110). If the detected current exceeds sample size threshold 72, then it is known that sufficient blood is present in well 20 to hydrate the enzyme reactants positioned therein (decision box 112). If not, an error is indicated. If yes, the procedure continues, with microprocessor 42 causing the removal of excitation voltage $V_e$ from contact A (box 114).

After expiration of the incubation time period, microprocessor 42 causes excitation supply 23 to apply an excitation voltage (trace 76 in FIG. 3) to contact A (box 116). The application of $V_e$ level 76 causes a reversal of the enzymatic reaction referred to above and results in a current flow (shown by trace 78 in FIG. 3) between excitation electrode 14 and sense electrode 12. At this point, a "measurement period" commences and, as shown in FIG. 5, a number of current measurements 82, 84, 86 etc, are taken (until measurement 88) and the results are stored (see FIG. 5 and box 118, FIG. 7). Each measurement is taken after a time interval associated with count k. In FIG. 5, fourteen such time intervals are shown, with current measurements not being taken until the end of the second interval to prevent the resulting current reading from exceeding a maximum measurable current.

During the time when current values 82, 84, 86 etc. are being measured, a "delta" fail/safe calculation occurs after the second current measurement and then after each succeeding current measurement (box 120). In essence, it is known that if trace 78 follows a Cottrell curve, it monotonically decreases and each succeeding current measurement is less than a preceding current measurement by at least a predetermined delta fail/safe threshold value. That value is obtained from ROM key 48 and is accessed by microprocessor 42.

As shown in decision box 120, microprocessor 42 determines that each succeeding sense current $i_k$ is less than or equal to a preceding sampled current value ($i_{k-1}$) plus the delta fail/safe threshold value. If a succeeding sense current value does not meet that test, an abort message is sent to the user (via display 44) based on the determination that the current waveform is not exhibiting an expected monotonic relationship. This test is repeated for each succeeding current sample, including last current sample 88. Until then, the procedure repeats as shown by decision box 124.

Once current measurement 88 has been taken, the procedure moves to a "current sum" fail/safe determination. The current sum fail/safe procedure performs another check on the Cottrell response during the measurement period. When the final current sample 88 is acquired, it is multiplied by two constants (i.e. values) that are accessed by microprocessor 42 from ROM key 48. The results of the multiplication are then used as two limit values against which a sum of all of sensed currents 82, 84, 86 etc. is tested. If the sum falls between the two limits, it is known that trace 78 follows the Cottrell relationship. These actions are illustrated in boxes 122, 124, 126 and 128 in FIG. 7. Current sum $I_{sum}$ is calculated as follows (box 122)

$$I_{sum} = \sum_{k=1}^{m} i_k$$

where $i_k$ is one of m current samples.

Then it is determined whether $I_{sum}$ falls within upper and lower limits as follows (box 128)

$$i_m K_u > I_{sum} > i_m K_l$$

where
$K_l$ is the lower limit constant,
$K_u$ is the upper limit constant, and
$i_m$ is the final current sample.

If the test shown in decision box 128 is not met, an abort signal is issued. However, if the test is met, then a glucose calculation follows (box 130), with the result displayed to the user.

The basis of the current sum fail/safe test can be determined from the following proof.

Initially, consider the ratio r $$r = \frac{\sum_{k=1}^{m} i_k}{i_m} \quad (A)$$

of all sensed currents to the final sensed current.

It is to be proved, for any current trace with a Cottrell behavior, that the ratio has the same value $r_{cottrell}$ independent of any factors (including glucose concentration).

The Cottrell response characteristic is given by equation (B):

$$i_{cottrell}(t) = \frac{nFA\sqrt{D}}{\sqrt{\pi}\sqrt{t}} C \quad (B)$$

where:
n is the number of electrons freed per glucose molecule,
F is Faraday's Constant,
A is the working electrode surface area,
t is elapsed time since application of excitation,
D is the diffusion coefficient,
C is the glucose concentration.

Of the above-listed parameters, n and F are constants, A is determined by strip design, D and C while possibly varying from trace to trace, stay constant within the duration of a current trace for a given test. Thus, all parameters of equation B, except for time t are constant for a given current trace.

By replacement of current terms $i_k$ in equation (A) by their Cottrell representations from equation (B), the following expression is obtained $$r_{cottrell} = \frac{\sum\limits_{k=1}^{m} \frac{nFA\sqrt{D}}{\sqrt{\pi}\sqrt{t_k}} C}{\frac{nFA\sqrt{D}}{\sqrt{\pi}\sqrt{t_m}} C} \quad (C)$$

By removing the constant terms in the numerator and denominator, expression (C) becomes:

$$r_{cottrell} = \frac{\sum\limits_{k=1}^{m} \frac{1}{\sqrt{t_K}}}{\frac{1}{\sqrt{t_m}}} \quad (D)$$

Considering expression (D), it can be concluded that if a trace has Cottrell behavior, then the ratio r shown in equation A calculated with this trace's currents must be equal to $r_{cottrell}$. Inversely, if a trace has non-Cottrell behavior, then the corresponding ratio r from equation (A) is different from $r_{cottrell}$.

The Cottrell model (B), while very accurate, is still a model, therefore in practice there might be a small difference between r and $r_{cottrell}$ for a trace with Cottrell behavior. In order to allow for this difference the calculated ratio r, instead of checking on an exact equality to $r_{cottrell}$, is compared with an upper limit $r_{cottrell} + \epsilon_u \cdot r_{cottrell}$ and a lower limit $r_{cottrell} - \epsilon_l \cdot r_{cottrell}$, where $\epsilon_u$ and $\epsilon_l$ are small numbers.

The following inequality $$r_{cottrell} + \epsilon_u\, r_{cottrell} > r > r_{cottrell} - \epsilon_l\, r_{cottrell}$$

is equivalent to the following comparison:

$$(r_{cottrell} + \epsilon_u r_{cottrell})^* i_m > \sum_{k=1}^{m} i_k > (r_{cottrell} - \epsilon_l r_{cottrell})^* i_m \quad (E)$$

by denoting $$K_u = (r_{cottrell} + \epsilon_u\, r_{cottrell}) * i_m$$

$$K_l = (r_{cottrell} - \epsilon_l\, r_{cottrell}) * i_m$$

inequality (E) becomes inequality (F)

$$K_u > \sum_{k=1}^{m} i_k > K_l \qquad (F)$$

which is used as a failsafe test as shown in FIG. 7 (Box 128).

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A biosensing meter for receiving a sample strip that includes electrically isolated excitation and sense electrodes and a sample well bridging thereacross, with an analyte reactant resident therein, said biosensing meter comprising:

excitation supply means for applying an excitation potential to said excitation electrode;

sense amplifier means connected to said sense electrode for producing an output signal when a volume of a biological fluid is placed in said sample well and creates a current path between said excitation and sense electrode;

processor means coupled to said sense amplifier means for first, testing if said output signal exceeds a first threshold value and second, testing if said output signal thereafter exceeds a second, larger threshold value, an output signal that exceeds said first threshold value recognized as an indication of said volume in said sample cell, an output signal that exceeds said second larger threshold recognized as an indication that said volume will enable a subsequent determination to be made for an analyte in said biological fluid, said processor means only enabling said subsequent determination after said second, larger threshold has been exceeded by said output signal.

2. The biosensing meter as recited in claim 1 wherein said processor performs said second test only after a preset delay, said preset delay enabling said volume of biological fluid to wet said analyte reactant.

3. The biosensing meter as recited in claim 1, wherein said amplifier means produces a leakage signal value prior to placement of said volume of biological fluid in said sample well, said leakage signal value indicative of a leakage current between said excitation and sense electrodes, said biosensing meter further comprising:

key means containing a memory with stored values, said stored values including a leakage current threshold value, a drop detect threshold value, and a said second threshold value;

whereby said processor means determines if said leakage current value exceeds said leakage current threshold value and, if not, adds said leakage current value to said drop detect threshold value to derive said first threshold.

4. The biosensing meter as recited in claim 3 wherein said processor means employs said second threshold value from said key means to determine that said volume amount will enable said subsequent determination.

5. A biosensing meter for receiving a sample strip that includes a pair of electrode means and an analyte reactant containing reaction zone bridging said pair of electrode means, said biosensing meter for determining whether a current through said reaction zone varies in accordance with a Cottrell relationship, said meter comprising:

sense amplifier means for obtaining a plurality of successive readings of current in said reaction zone over a plurality of measurement times, after a sample containing an analyte is placed in said reaction zone; and processor means for comparing each of a plurality of successive current readings with immediately previous current readings to test if each said successive current reading exhibits a smaller value than an immediately previous current reading, and if not, issuing a signal indicative of a failure of said test.

6. The biosensing meter as recited in claim 5, further comprising:

pluggable key means containing a memory with stored values, one such value being a delta change value; and whereby said processor means performs said test by summing said delta change amount, as accessed from said pluggable key means, with one said current reading and comparing said summed value with another said current reading.

7. A biosensing meter for receiving a sample strip that includes a pair of electrode means and analyte reactant containing reaction zone bridging said pair of electrode means, said biosensing meter for determining whether a current through said reaction zone varies in accordance with a Cottrell relationship, said meter comprising:

sense amplifier means for obtaining a plurality of successive values of current in said reaction zone over a plurality of m measurement times, after a sample containing an analyte is placed in said reaction zone; and processor means for summing said successive values of current and determining if a ratio of said summed values to a value of a current, determined at an m'th measurement time, falls within a set range, and if yes, proceeding to a further determination.

8. The biosensing meter as recited in claim 7, further comprising:

key means containing a memory with stored values, a pair of said values being upper ($K_u$) and lower ($K_l$) comparison constants, whereby said processor means employs said upper and lower comparison constants to establish said range.

9. In a system for measuring a current i passing through a reaction zone of a test cell, which current, in dependence upon the concentration of an analyte in the reaction zone, changes to follow one of a family of curves whose shape is defined by the Cottrell equation, a method for determining that said current is changing in accordance with the Cottrell equation, said method comprising the steps of:

(a) measuring said current i at a plurality of measurement times $t_n$, $t_{n+1}$, $t_{n+2}$ ... $t_m$ to derive current values $i_n$, $i_{n+1}$, $i_{n+2}$ ... $i_m$;

(b) comparing each current value with an immediately succeeding current value to test if said succeeding current value is smaller by at least a threshold value;

(c) if the test of step b is not fulfilled, providing a signal indicating that said measured current in said test cell is not changing in accordance with said Cottrell equation.

10. In a system for measuring a current i passing through a reaction zone of a test cell, which current, in dependence upon the concentration of an analyte in the reaction zone, changes to follow one of a family of curves whose shape is defined by the Cottrell equation, a method for determining that said current is changing in accordance with the Cottrell equation, said method comprising the steps of:

(a) measuring said current i at a plurality of measurement times $t_n$, $t_{n+1}$, $t_{n+2}$ ... $t_m$ to derive current values $i_n$, $i_{n+1}$, $i_{n+2}$ ... $i_m$;

(b) summing said current values $i_n$ through $i_m$ and determining if a ratio of said sum to $i_m$ falls within a constant range; and, if not (c) providing a signal indicating that said measured current in said test cell is not changing in accordance with said Cottrell equation.

* * * * *